United States Patent [19]

Meyer et al.

[11] Patent Number: 4,703,781

[45] Date of Patent: Nov. 3, 1987

[54] METHOD FOR MANUFACTURING A PREFILLED SINGLE-DOSE SYRINGE AND INSTALLATION FOR CARRYING OUT THE METHOD

[75] Inventors: Gabriel Meyer; Ernst Howald, both of Vesenaz, Switzerland

[73] Assignee: Cosmonor S.A., Vesenaz, Switzerland

[21] Appl. No.: 833,392

[22] PCT Filed: May 15, 1985

[86] PCT No.: PCT/CH85/00080

§ 371 Date: Jan. 10, 1986

§ 102(e) Date: Jan. 10, 1986

[87] PCT Pub. No.: WO85/05269

PCT Pub. Date: Dec. 5, 1985

[30] Foreign Application Priority Data

May 16, 1984 [CH] Switzerland ............... 2399/84

[51] Int. Cl.⁴ .................................. B67C 7/00
[52] U.S. Cl. ............................ 141/5; 141/11; 141/83; 141/95; 141/350; 141/70

[58] Field of Search ...................... 141/1-12, 141/37-70, 18-27, 329, 330, 94-96, 83, 129-191

[56] References Cited

U.S. PATENT DOCUMENTS 4,457,877 7/1984 Love et al. ................ 141/70

Primary Examiner—Houston S. Bell, Jr.
Attorney, Agent, or Firm—Frost & Jacobs

[57] ABSTRACT

The present invention relates to a method for manufacturing a prefilled single-dose syringe.

It comprises a station (12) for supplying the ampoules (2), a station (13) for pregassing the ampoules (2), a station (14) for filling-gassing the ampoules (2), a station (15) for supplying the injector bodies (3), equipped with their needle-holder covering cap (4), a station (16) for assembling the ampoules (2) and the injector bodies (3), a station (19) for final control of the syringe (1), a station (22) for release of the syringes accepted by the final control station, a station (20) for quantitative control of gassing of the syringes, a station (21) for qualitative control of gassing of the syringes.

25 Claims, 21 Drawing Figures

METHOD FOR MANUFACTURING A PREFILLED SINGLE-DOSE SYRINGE AND INSTALLATION FOR CARRYING OUT THE METHOD

The present invention relates to a method for manufacturing a prefilled single-dose syringe, comprising on one hand an ampoule open at one end, provided with a neck of contricted section for containing a medicine to be injected, and on the other hand an injector composed of a capsule adaptable to the ampoule neck and a piston-valve solid with the capsule and adapted for insertion into the ampoule, wherein the ampoule containing the medicine to be injected and the injector are conveyed via two separate paths to the same assembling station, these two components are positioned above one another and brought together for assembly, and wherein gassing of the ampoule or of the ampoule and of the injector is effected prior to assembly of these components, in said assembling station.

It likewise relates to an installation for manufacturing a prefilled single-dose syringe, for carrying out said method, comprising means for gassing the ampoule or the ampoule and the injector, before or during assembly of these two components.

There are numerous known automatic installations for assembling disposable syringes which generally consist of a syringe body and a piston engaged in this body. These installations are generally of conventional design, the precautions to be taken to avoid contamination of the components as well as to control the assembly are well known and the means for their implementation are relatively simple.

It is quite different in the case of prefilled syringes of the single-dose type having components which must be mechanically manipulated with particular precision and care and where new operations such as filling of the ampoules take place in the course of assembly.

The requirements with regard to filling are extremely strict, given that the objective to be achieved consists in introducing the medicine into the syringe and in hermetically sealing the latter, in such a manner that the atmosphere above the medicine in the syringe consists exclusively of a gas selected as a function of the medicine, for example a neutral gas, that is to say it should be free of solid particles, of contaminants, of oxygen or oxygenous substances.

To meet these requirements, one could of course use the well known techniques consisting in mounting the installation in a room with a controlled neutral atmosphere. Due to the installation's costs and the important technical means for its implementation, the choice of such a solution constitutes a serious handicap for the widespread use of prefilled single-dose syringes.

Another technique has been utilized to effect gassing of the ampoule after it has been filled and during mounting of the piston in certain prefilled syringes comprising an ampoule which in fact constitutes the body of the syringe and a piston which closes off one of the extremities of this body. This technique consists in squeezing the piston between two jaws so as to reduce its diameter, and in injecting a selected gas between the inner wall of the syringe body and the piston, on one side of the latter, in such a manner that the gas may escape on the other side.

Such a procedure does not ensure that the gas does not drive solid particles or oxygen towards the interior of the syringe body and does not permit an overpressure of the gas to be built up within the syringe.

Moreover, the present techniques do not allow this ampoule gassing operation to be controlled qualitatively, nor quantitatively, and consequently to stop production in case defects are observed.

Another requirement imposed on the method is that of controlling the manufactured products. It is known that the sealed ampoules presently containing most medicines intended for injection, are subjected to an optical control which permits in principle to verify the absence of solid particles, and a control of airtightness called "blue bath control" which consists in immersing the ampoule in a coloured liquid bath and in verifying each ampoule individually to detect the possible presence of coloured liquid in the medicine ampoule.

Needless to say this control is fastidious and costly and its effectiveness may be doubtful in some cases.

In the present invention it is proposed to palliate these drawbacks of the known systems and to develop a simple and efficient method of manufacturing prefilled single-dose syringes, which at the same time meets the strictest requirements with regard to filling as well as control in the course of manufacturing and final control of the products.

To this end, the method according to the present invention is characterized in that gassing is effected by producing within a cavity containing the entire ampoule a stream of gas circulating from the bottom upwards and sweeping the outer walls of the ampoule, and by creating a flow of gas sweeping through the channels of the injector, in that a qualitative and/or quantitative gas control is effected during or after gassing, and in that a final control of the syringe is effected after assembling the components, by exerting a thrust on one of these components and by controlling at least the return movement of this component towards its initial position.

According to a preferred mode of carrying out the invention, at least one phase for gassing the injector comprises sweeping the channels with an ascending flow of gas initially rising above the liquid contained in the ampoule, which is driven towards the channels when the injector is set in place.

The gas stream sweeping the external walls of the ampoule preferably has a speed greater than the speed of a laminar flow in which the installation is placed, and which is capable of keeping away contaminating particles.

According to a particularly advantageous mode of carrying out the invention, the sweeping gas stream is produced by delivering into the cavity containing the ampoule a predetermined amount of selected gas stored in a measuring chamber.

According to another advantageous mode, the sweeping gas stream is produced by continuously supplying a selected gas to the cavity containing the ampoule.

To create an overpressure within the ampoule, the cavity containing the ampoule may be closed off and the sweeping gas stream is thus produced at a pressure greater than atmospheric pressure.

To effect gassing of the injector, a descending sweeping gas stream is produced through the channels of the injector during at least one phase of the operation.

One may likewise maintain the injector in a chamber containing a selected gas, while being set in place on the ampoule.

According to an advantageous mode, gas control is effected statistically by punctual interventions at a determined frequency.

The final control of the syringes is preferably effected by exerting a given force axially on the ampoule or on the injector which have been previously assembled, and determining both the value of the relative penetration of these two components and the value of the return movement of these components to their initial position.

To complete the measurement and facilitate interpretation of the results, one may likewise determine the algebraic sum of the two values of the relative penetration and the return movement of the components to their initial position.

Said force is preferably exerted by means of an inertia weight of predetermined mass.

According to a preferred mode of carrying out the installation according to the invention, the gassing cavity has a depth greater than the height of the ampoule, and the installation comprises means for bringing a selected gas into this cavity and means for creating a sweeping stream of this gas, circulating from the bottom upwards between the walls of the cavity and those of the ampoule.

The gassing cavity advantageously comprises a measuring chamber arranged under the gassing cavity, this measuring chamber being fed with a selected gas and initially containing a predetermined volume of this gas at a given pressure.

To permit transport of the ampoules, the gassing cavity is arranged in a central support and transfer unit, and this central unit has the form of a circular rotating table or a rectilinear table with linear displacement.

The central support and transfer unit preferably comprises several cavities, each of these cavities consisting of a recess provided at the periphery of said unit and comprising means for selectively closing this recess to form a cylindrical cavity.

According to a particular arrangement, the central support and transfer unit is divided into two adjacent blocks of which one is fixed and the other is mobile in translation, each of these blocks comprising a series of recesses disposed so that they may be brought to face one another whereby the ampoules and/or the injectors and/or the syringes may be transferred from one recess to another, and linearly displaced with the block which is mobile in translation.

According to another arrangement, the central support and transfer unit is associated with a second transport unit, and comprises a series of peripheral recesses each having a rotary door adapted to cooperate with the corresponding recess to form said gassing cavity.

The means for final control preferably comprise two dimension sensors, one of which is mounted on a fixed frame, and the other on a slide which is axially mobile with respect to this fixed frame.

Said means for final control advantageously comprise three indicators arranged to respectively indicate the relative penetration of the ampoule and the injector, the return of the injector with respect to the ampoule and the algebraic sum of the two preceding values.

The means for effecting quantitative control of the gas contained in the ampoule preferably comprise a volume gauge and means providing communication between the interior of the ampoule and this gauge.

The means for effecting qualitative control of the gas contained in the ampoule preferably comprise a particle counter and a partial gas pressure detector.

The gassing cavity is advantageously connected to a partial gas pressure detector and/or a particle counter.

The present invention will be better understood with reference to the described examples of embodiments and to the accompanying drawings wherein.

Figure 1A:
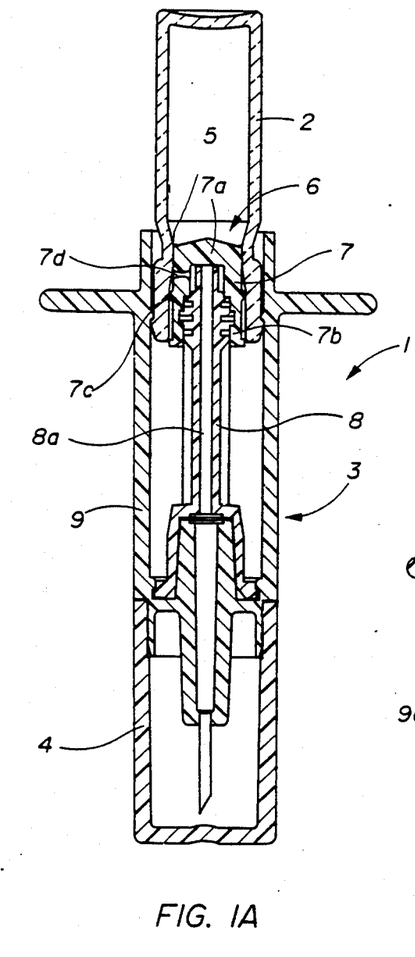
FIG. 1A represents an axial sectional view of a first embodiment of a prefilled single-dose syringe to be assembled by the method and installation according to the invention.

FIG. 1A represents a first embodiment of a prefilled single-dose syringe 1 which is to be made by the method defined above. It is essentially composed of an ampoule 2, an injector 3 and a needle-holder covering cap 4. The ampoule 2 comprises a neck 5 of constricted section.

The injector comprises a piston-valve 6 composed essentially of a flexible stoppering member 7 mounted on a rigid stiffening member 8 and a capsule 9 solid with the piston-valve 6 and adaptable over the ampoule neck. The flexible stoppering member 7 comprises a piston head 7A solid with an annular skirt 7b provided with at least one sealing flange 7C. A radial channel 7d, provided through the annular skirt communicates with an axial channel 8a provided in the rigid stiffening member 8. An ampoule-protecting cover 4' may be adapted onto the ampoule and fixed by removable means (not shown) to the capsule 9.

Figure 1B:
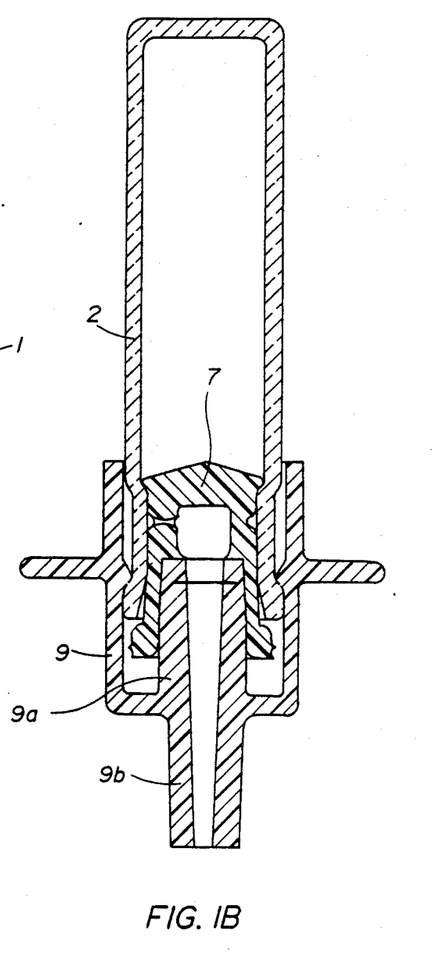
FIG. 1B represents an axial section of a second embodiment of a prefilled single-dose syringe to be assembled by the method and installation according to the invention.

FIG. 1B represents a second embodiment of a prefilled single-dose syringe which is to be made by the above method. It is essentially composed of an ampoule 2 containing a liquid medicine under the pressure of a selected gas. The flexible stoppering member 7 is directly mounted on a short stiffening member 9a solid with the capsule 9 and prolonged by a needle-holder nozzle 9b.

Figure 2:
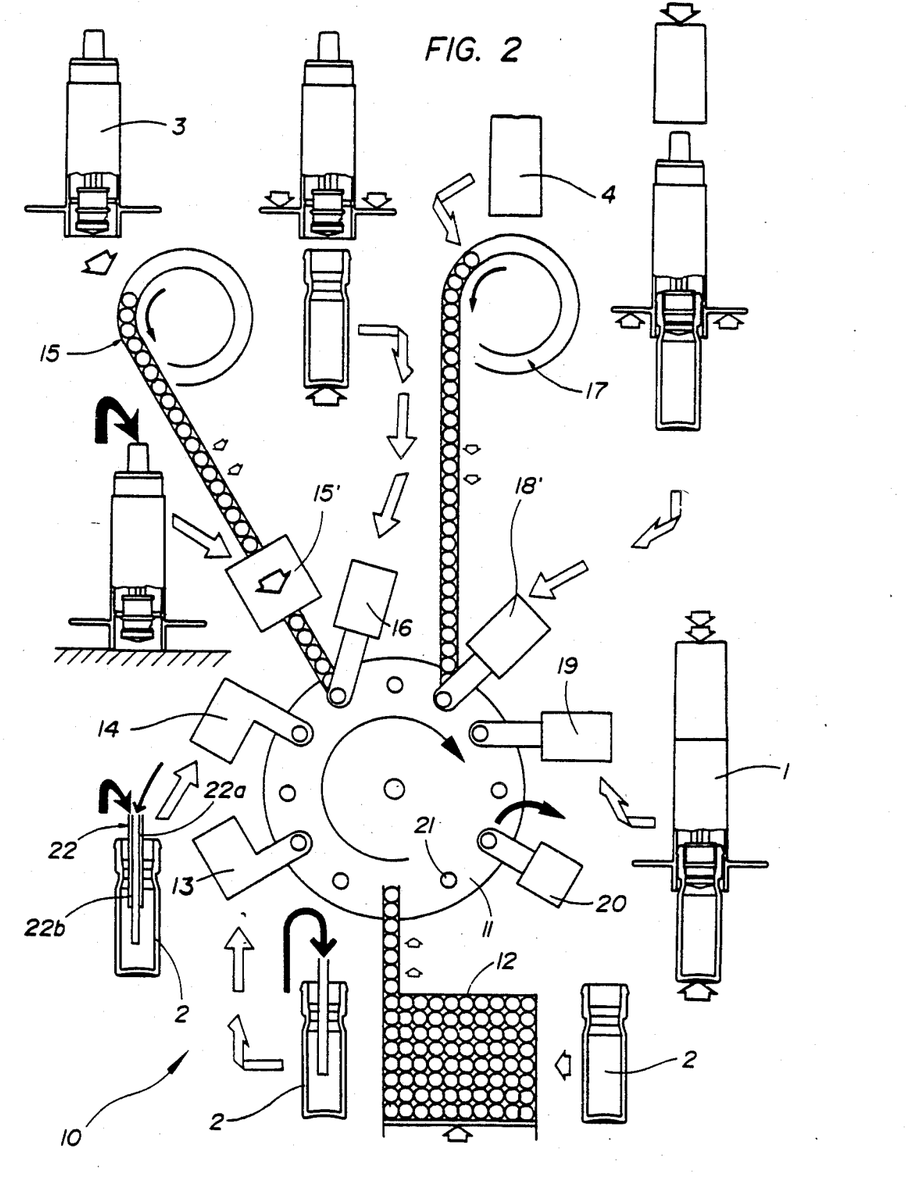
FIG. 2 represents a schematic view of a first embodiment of the installation according to the invention.

FIG. 2 illustrates schematically the installation 10 for manufacturing a prefilled single-dose syringe such as previously defined. This installation essentially comprises a central unit 11 for support and transfer of the components supplied to and treated in a series of work stations which, in the example illustrated by the figure, are the following:

(a) a station 12 for supplying the ampoules, (b) a station 13 for pregassing the ampoules 2, (c) a station 14 for filling-gassing the ampoules 2, (d) a station 15 for supplying the injectors, coupled with a station 15' for gassing the injectors, (e) a station 16 for assembling the ampoules 2 and the injectors 3, (f) a station 17 for supplying the needle-holder covering caps 4, (g) a station 18 for positioning said needle-holder covering caps 4, (h) a final control station 19 for the syringe 1, and (i) a station 20 for releasing the syringes accepted by the final control station.

In this embodiment, the ampoules 2 are accomodated in cavities 21 provided along the periphery of the central support and transfer unit 11. The ampoules are thereby the directing members driving the injectors after passage into the station 16.

This choice permits, as will be described later in more detail, a gassing of the ampoules to be effected during the entire ampoule positioning phase and, in certain cases, a gas pressure greater than atmospheric pressure to be maintained above the liquid medicine. Pregassing in the station 13 has the object of "washing" the ampoules by means of a selected gas such as for example $CO_2$, which is the most generally used. Filling-gassing is effected in the station 14 preferably by means of a double needle 22 having a central channel 22a serving to fill the ampoule and having the peripheral annular channel 22b ensuring the gas supply for gassing the ampoule.

Figure 3:
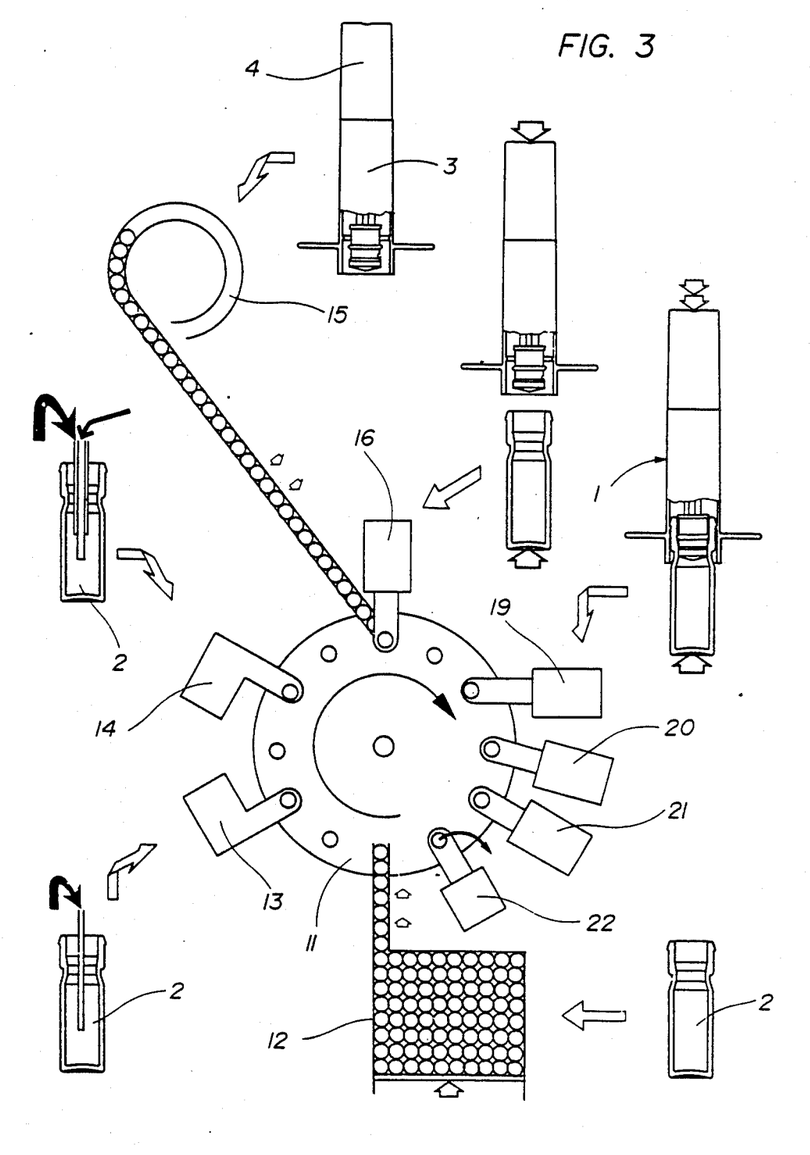
FIG. 3 represents a schematic view of another embodiment of the installation according to the invention.

A variant of this installation is illustrated in FIG. 3. This installation comprises as previously a central unit 11 for support and transfer of the components, as well as the following stations:

(a) a station 12 for supplying the ampoules 2, (b) a station 13 for pregassing the ampoules 2, (c) a station 14 for filling-gassing the ampoules 2, (d) a station 15 for supplying the injectors 3, equipped with their needle-holder covering cap 4, (this station is thus, in this case, not coupled with a station for gassing the injectors), (e) a station 16 for assembling the ampoules 2 and the injectors 3, (f) a station 19 for final control of the syringe 1, (g) a station 20 for quantitative control of gassing the syringes, (h) a station 21 for qualitative control of gassing the syringes, (i) a station 22 for releasing the syringes accepted by the final control station.

The stations 17 for supplying and 18 for positioning the needle-holder covering caps 4 have been eliminated, given that the injectors are supplied by the station 15, already equipped with said needle-holder covering caps.

It is evident that this variant in the form of the represented arrangement does not allow the injector to be gassed while it is being set in place on the ampoule.

Figure 4A:
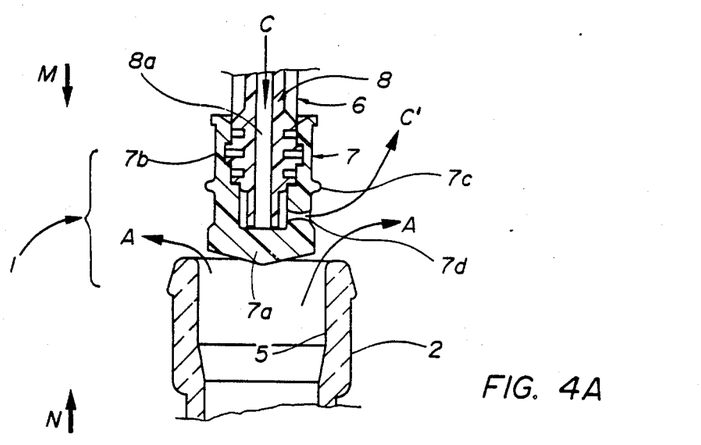
FIGS. 4A, 4B and 4C illustrate the three principal phases of setting the injector in place on the ampoule.
Figure 4B:
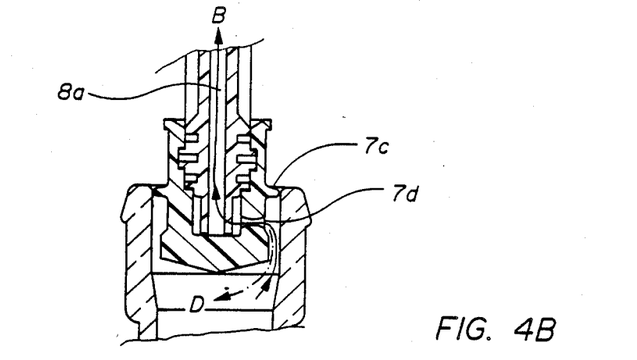
Figure 4C:
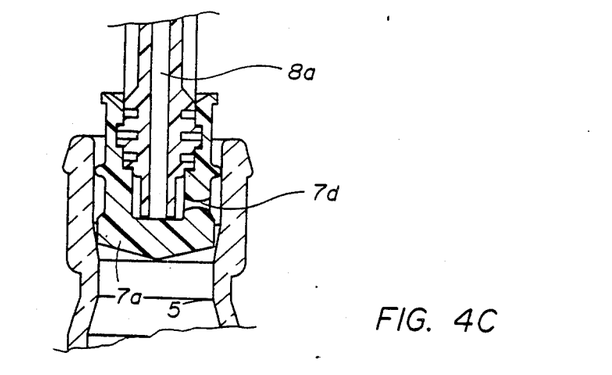

FIGS. 4A, 4B and 4C illustrate the three principal phases of setting the injector in place on the ampoule in the case where only the ampoule is gassed or in the case where two components, namely the ampoule and the injector, are simultaneously gassed.

These figures show the syringe 1 partially represented. The ampoule 2 pregassed in the station 13 is filled and gassed in the station 14. In the station 12, it has been previously introduced into a cavity which is likewise gassed (see detailed description below), in such a manner that a stream of selected gas flows from the bottom upwards around the ampoule, while preventing any penetration of particles and of air and in particular of oxygen into the ampoule. One can thereby assume that the inner ampoule space overlying the liquid medicine is entirely filled with the selected gas, when the injector is brought above the ampoule opening. When the injector is lowered in the direction of arrow M (or when the ampoule is pushed upwards in the direction of arrow N), the reduction of free volume produced by inserting the piston-head 7a causes an escape of gas in the direction of the arrows A. By virtue of Henry's law relating to equilibrium of partial pressures in gas mixtures, the oxygen contained in ambient air would tend, in the static state, to penetrate into the space overlying the liquid within the ampoule. To avoid such a migration of oxygen during and after filling the ampoule, a flow of selected gas is produced from the interior to the exterior. This flow creates a stream of sweeping gas preventing any penetration of air, and of oxygen in particular, as well as any penetration of solid particles into the ampoule.

This stream continues to take place until the moment when the sealing flange 7c enters into contact with the edge of the ampoule (see FIG. 4B). The first point of sealing is attained. If one continues to displace the ampoule and/or the injector with respect to one another, the volume which is supposed to be occupied by the gas overlying the medicine continues to be reduced. A part of this seleted gas escapes through the radial channel 7d and reaches the axial channel 8a, as is shown by the arrow B. This results in "rising" the injection channels by means of the selected gas and in avoiding any penetration of particles or of oxygen via this path.

If one continues to displace the ampoule and/or the injector towards one another, the piston-head 7a is engaged in the zone of the neck of constricted section to attain the second point of sealing illustrated in FIG. 4C. From then on, relative displacement of the ampoule and the injector, which reduces the volume of the gas overlying the liquid medicine, leads to an increase in the pressure of this gas within the ampoule. As soon as this second sealing point is attained, the radial channel is in fact closed off, which prevents any gas leakage via this path.

In practice, one will continue to push downwards the injector up to a position in which the piston head 7 undergoes maximum compression in the zone of constricted section of the ampoule neck, while the sealing flange or lip 7c remains positioned in the wide zone prolonging this constricted neck, in order to avoid a too great compression of this flange during the storage phase. This strong compression of the piston head constitutes in practice an excellent protection against migration of oxygen towards the interior of the ampoule during storage of the syringe.

The case decribed above corresponds in fact to the arrangement according to FIG. 3, that is to say that where the injectors are brought to the station 15, equipped with the needle-holder covering cap 4, and where one does not effect gassing of the injector when assembling this injector with the ampoule, for example because the injector has already been pregassed in a previous station.

In the case where such gassing is effected, one injects selected gas into the axial channel 8a. This gas "rinses" the axial channel and next the radial channel 7d and initially escapes in the direction of the arrow C'. When one is in the stage illustrated in FIG. 4b, the selected gas injected through the axial channel is forced to penetrate into the interior of the ampoule in the direction of arrow D. By this means, it becomes possible, among other things, to create an adjustable overpressure which may be relatively great within this ampoule. As soon as the piston head 7a reaches the position illustrated in FIG. 4C, the injection of selected gas into the interior of the ampoule via the axial channel 8a and channel 7d is stopped.

As previously mentioned, it is necessary to develop a flow of inert gas escaping from the interior of the ampoule to avoid penetration of air or solid particles into the ampoule at the time when the injector is set in place. The risk of accidental penetration of particles and oxygen into the selected gas atmosphere overlying the medicine is further minimized if one operates in a closed chamber filled with the selected gas. Similar conditions may be achieved when the ampoule is entirely accomodated in a cylindrical cavity and the space between the inner walls of the cavity and the outer walls of the ampoule is swept by an ascending stream of selected gas.

Figure 5:
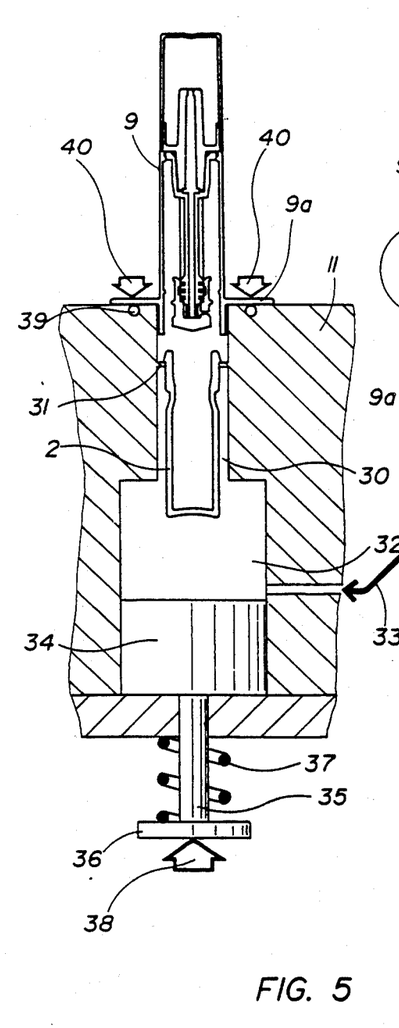
FIG. 5 is a partial sectional view of an embodiment of the central support and transfer unit, more particularly illustrating the ampoule-receiving cavity.

To this end, the central support and transfer unit 11, illustrated in FIG. 5, likewise called rotating or linear table, comprises cavities 30 in which the ampoules 2 are accomodated, suspended on lateral stops 31. Each of these cavities communicates with a chamber 32 supplied with selected gas, represented by the arrow 33, originating from a source of gas under pressure. This chamber 32 contains a piston 34 arranged to be actuated by a rod 35 provided with a bearing plate 36 which is acted upon by a pressure spring 37 and a force symbolized by the arrow 38.

When the piston 34 is driven upwards, it cuts off the supply of selected gas and expels the gas from the chamber into the cavity 30 while producing a sweeping stream around the ampoule walls. When the injector is brought above the ampoule, one finds the configurations of FIGS. 4A, 4B and 4C. Sealing joints 39 are provided around the upper opening of the cavities 30, in order to ensure sealing between the capsule 9 and the table 11, and to permit injecting the selected gas with overpressure into the ampoule. Sealing is maintained by means of a pressure applied in the direction of the arrows 40 on the fingergrips 9a of the capsule 9. The piston 34 has a dual object: in a first phase it produces a flow of selected gas around the ampoule and in a second phase it drives the ampoule upwards to cause assembling of the injector with the ampoule.

Figure 6:
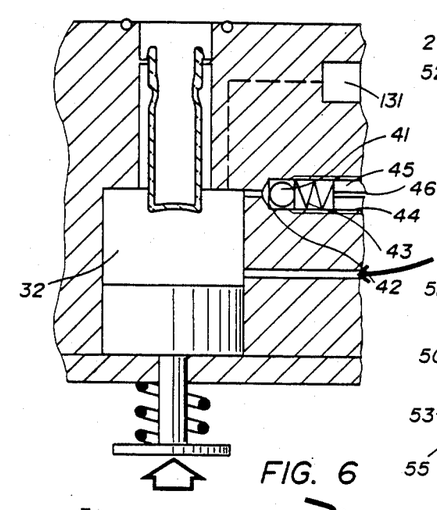
FIG. 6 represents a sectional view of another embodiment of the ampoule-receiving cavities.

The cavity 30 provided in the table 11 and illustrated in FIG. 6 differs from the previous one in that it comprises an overpressure valve communicating with the chamber 32. This valve comprises a ball 41 maintained in bearing relationship upon a seat 42 by a spring 43 set in a bore 44 by a screw 45 with a channel 46 therethrough. The pressure of the spring 43 adjustable by the screw 45 permits to determine a maximum pressure of the gas contained in the chamber 32, at the end of the stroke of the piston, and consequently the maximum pressure of the gas contained in the ampoule. It likewise differs in that it comprises a device of the type described in detail with reference to FIG. 17, to permit detection of the partial oxygen pressure and/or solid particles.

Figure 7:
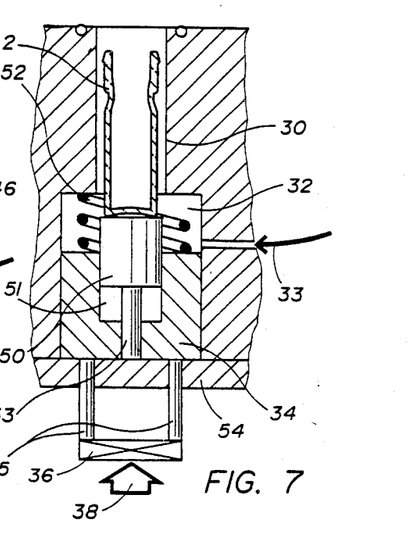
FIG. 7 represents a variant of the assembling mechanism associated with the ampoule-receiving cavities.

FIG. 7 illustrates another arrangement of the cavity 30 containing the ampoule 2 and of the mechanism for assembling the latter with the injector. In this example, the cavity does not comprise any stop for holding the ampoule, which rests on a pusher accomodated within the chamber 32.

This chamber comprises as before a piston 34 which, in this case, comprises a cavity 51 in which the pusher 50 is partly accommodated. A compression spring 52 is disposed in the chamber 32 while bearing, on one hand upon the upper surface of the piston 34, and on the other hand upon the upper surface of the chamber 32. The pusher 50 rests on a vertical fixed rod 53 solid with a base plate 54 or bearing upon the latter. This base plate preferably has two rods 55 passing therethrough which are provided as before with a bearing plate 36 upon which a force symbolized by the arrow 38 can act.

The ampoule 2 is initially accomodated in the cavity 30 and bears upon the pusher 50. When the force 38 acting upon the bearing plate 36 pushes the piston 34 upwards, the selected gas supply represented by the arrow 33 is firstly cut off, then the gas contained in the chamber 32 is progressively expelled between the outer walls of the ampoule 2 and the inner walls of the cavity 30. When the piston 34 is sufficiently raised for the bottom of the cavity 51 to come to bear upon the base of the pusher 50, the piston 34 drives the pusher 50 and exerts a vertical ascending thrust on the ampoule 2, this thrust being sufficient to cause assembling of the ampoule with the injector (not shown). The spring 52 acts as a return spring serving to drive the piston 34 to its initial position, the pusher returning automatically to its starting position.

Figure 8:
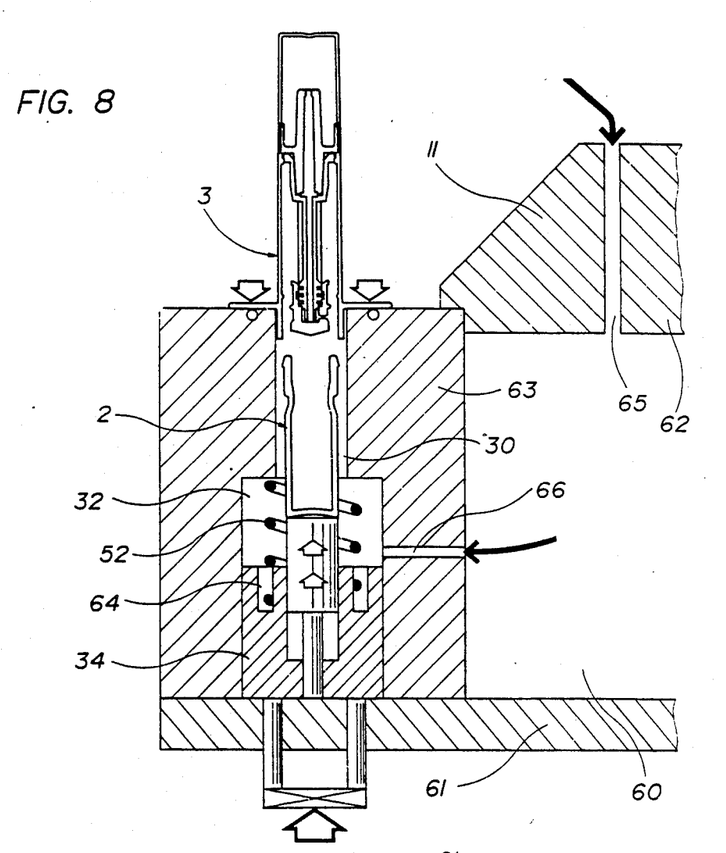
FIG. 8 represents a transversal sectional view of a particular embodiment of the central ampoule support and transfer unit.

In the example illustrated in FIG. 8 the central unit 11 for support and transfer of the ampoules 2 and of the injectors 3 comprises a central cavity 60 defined by a base plate 61, a covering plate 62 and an annular block 63 in which the cavities 30 are provided to receive the ampoules 2. Apart from the existence of an annular cavity 64 provided at the upper surface of the piston 34, which cavity serves to partially accomodate the compression spring 52, the mechanism for assembling the ampoules with the injectors, which simultaneously constitutes the device for expelling the selected gas, is identical with that previously described with reference to FIG. 7.

The selected gas is injected into the central cavity through a duct 65 passing through the covering plate 62. A duct 66 is provided passing through the annular block 63 to provide communication of the cavity 60 with the chamber 32 located under the cavity 30.

Figure 9:
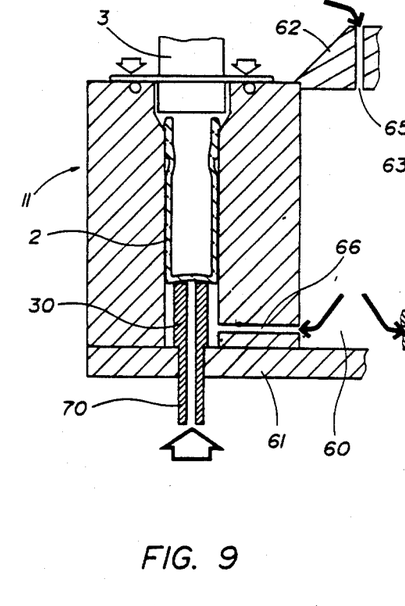
FIG. 9 represents a variant of this central support and transfer unit.

FIG. 9 illustrates a variant of the arrangement according to FIG. 8, in which the gas measuring chamber 32, utilized to produce laminar flow around the ampoule walls, has been eliminated. In this arrangement the selected gas is introduced into the central cavity 60 through the duct 65 passing through the covering plate 62. Gassing of the cavities 30 containing the ampoules 2 is effected in a continuous manner (and no longer discontinuously as in the preceding arrangements) through the supply duct 66 which provides communication of the cavity 60 with the cavity 30. The mechanism for assembling the ampoules with the injectors consists in this case of a pusher 70 passing through the base plate 61 of the central support and transfer unit 11.

Figure 10:
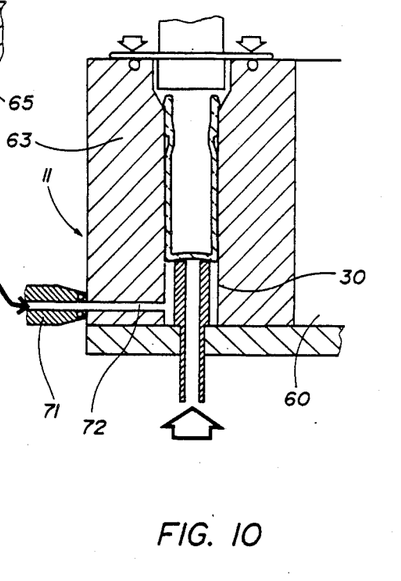
FIG. 10 represents another embodiment of this central ampoule support and transfer unit, more particularly illustrating a mode of bringing selected gas into the cavity containing the ampoules.

FIG. 10 illustrates another arrangement in which the central cavity 60 for storing the selected gas has been eliminated and replaced by external supply means 71 connected to a duct 72 which communicates with the cavity 30 provided in the annular block 63 of the central unit 11.

Figure 11:
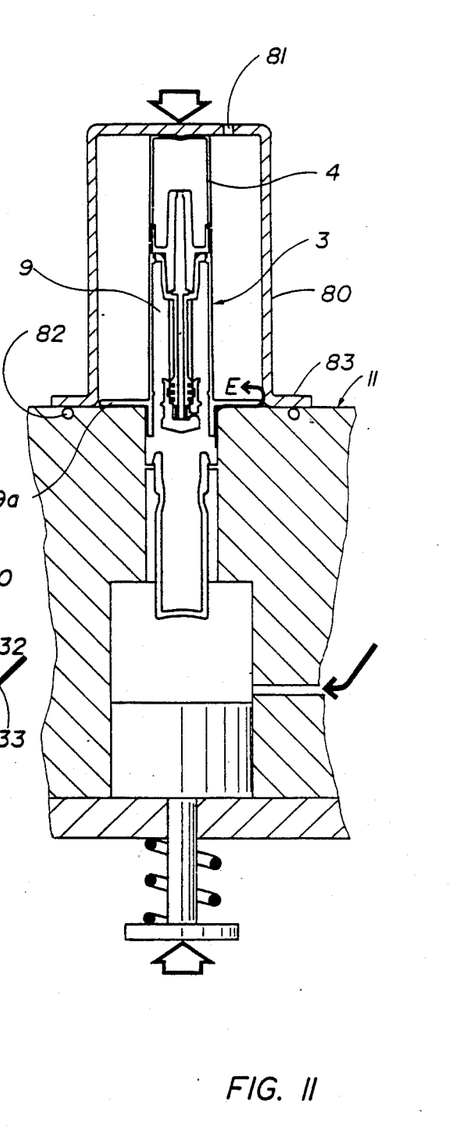
FIG. 11 illustrates an embodiment of the installation according to the invention, and more particularly a variant wherein a protective bell is provided covering the injector.

An interesting variant of the installation such as illustrated in FIG. 3 is represented in FIG. 11. According to this arrangement, a bell-shaped hood 80 is disposed on top of the injector 3, to maintain the latter in an enclosure essentially containing a selected gas. This enclosure advantageously comprises an opening 81 permitting the escape of surplus gas contained within the enclosure 80. Sealing joints 82 are provided under the rim of this enclosure in order to ensure an airtight closure between this rim 83 and the upper surface of the central unit 11. On the other hand, no sealing joint is provided at the level of the fingergrips 9a of the capsule 9, which permits flow of the selected gas contained in the cavity 30 towards the interior of the enclosure 80 in the direction of the arrow E.

This enclosure 80 has been mounted by way of example onto an installation in accordance with the arrangement of FIG. 5. It is however evident that such an enclosure may be mounted on any other installation described above, given that the presence of this enclosure has the object of creating a selected gas atmosphere around the injector during the phase of assembling the ampoule with the injector.

Generally speaking, the object of gassing the ampoules, as well as possible gassing of the injectors is to prevent particles or the oxygen in air from penetrating into the selected gas atmosphere overlying the liquid medicine contained in the ampoule. To avoid such penetration, one creates in all of the previously mentioned cases an ascending stream of a selected, sterile, filtered and clean gas in the cavity containing the ampoule, and one determines the speed of this ascending stream in such a manner that it is higher than that of the laminar flow in which the whole installation is placed. Present regulations with regard to the control of medicines for injection impose a final optical control intended to determine the possible presence of particles in the liquid medicine. Gassing such as described in detail above constitutes an effective means for assuring the absence of solid particles in the medicine, which assurance, combined with the presence of a filter through which the liquid medicine is forced to pass before being injected, makes it possible to quite safely eliminate this obligation of final optical control. The installation such as described above may moreover comprise a particle detector integrated in the installation as well as a probe for measuring the partial pressure of oxygen contained in the atmosphere which is introduced into the ampoule, when filling with the medicine must be effected in an oxygen-free environment, in such a manner that one has at disposal at the time of filing and assembling the syringe all the necessary indications for rendering totally superfluous this final optical control costing much time and material.

Figure 12:
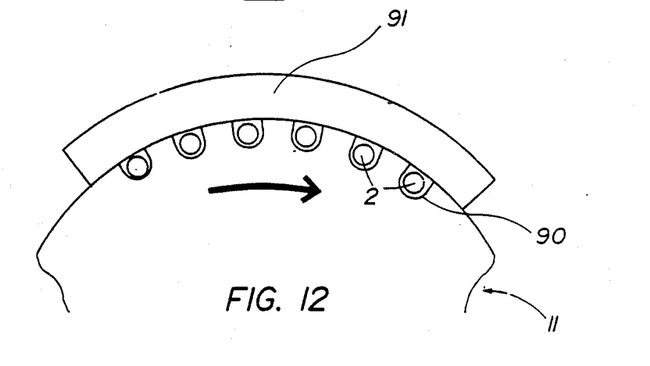
FIG. 12 illustrates an embodiment in which the central unit for support and transfer of the constituents consists of a rotating table.

To bring the ampoules to the different treatment stations, one may provide various transport devices. FIG. 12 illustrates an arrangement in which the central unit 11 for support and transfer of the components consists of a rotating table of which the peripheral surface is equipped with a series of recesses 90 designed to contain the ampoules 2, the latter being kept in the recesses by means of a fixed guide 91 which closes off these recesses.

Figure 13:
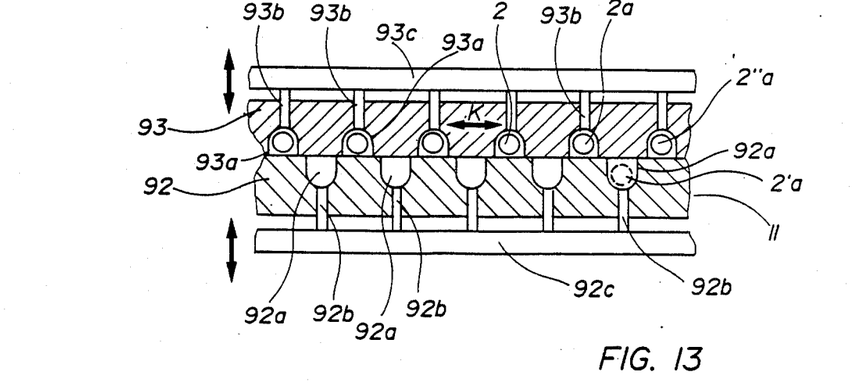
FIG. 13 represents another embodiment in which this central unit consists of a linear transfer unit.

FIG. 13 illustrates another arrangement in which the central support and transfer unit 11 consists of a linear transfer table consisting of a first fixed block 92 and a second block 93 movable in the direction of the double arrow K.

The two blocks 92 and 93 respectively comprise a series of recesses 92a and 93a which each cooperate with a pusher 92b and 93b, each series of pushers being connected by means of a strip 92c and 93c respectively. Cooperation between the different elements permits to make the ampoules 2 advance in a direction parallel to the direction of displacement of the block 93 by making them pass alternately from a recess 93a to a recess 92a, and vice versa. An ampoule 2a initially accomodated in a recess 93a is brought, when the block 93 is displaced from left to right, to face a recess 92a of the block 92. The corresponding pusher 93b pushes the ampoule 2a into the cavity 92a disposed opposite to it, where it will occupy the position 2'a represented in dashed lines. The block 93 will effect an inverse displacement from right to left until the following recess 93a will be facing the recess 92a containing the ampoule 2'a. The corresponding pusher 92b will drive the ampoule 2'a into this recess where it will occupy the position 2"a. This alternating displacement consequently permits to develop a linear or rotary displacement of the ampoules, and routing them to the different treatment stations.

Figure 13A:
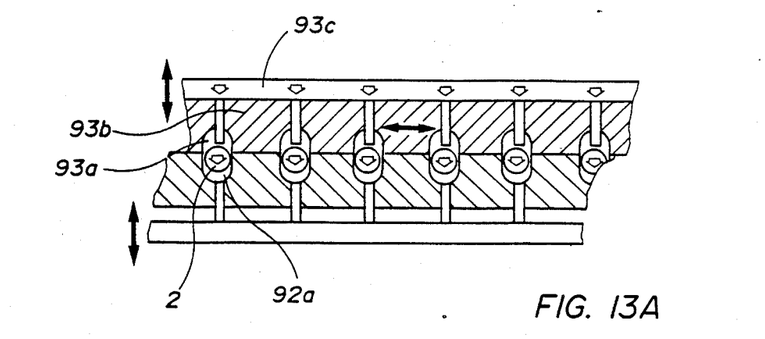
FIG. 13A represents an intermediate operating phase of the central support and transfer unit represented in FIG. 13.

FIG. 13A represents an intermediate phase in which the set of pushers 93b actuated by the corresponding strip 93c drives the set of ampoules from the recesses 93a to the oppositely disposed recesses 92a.

Figure 14:
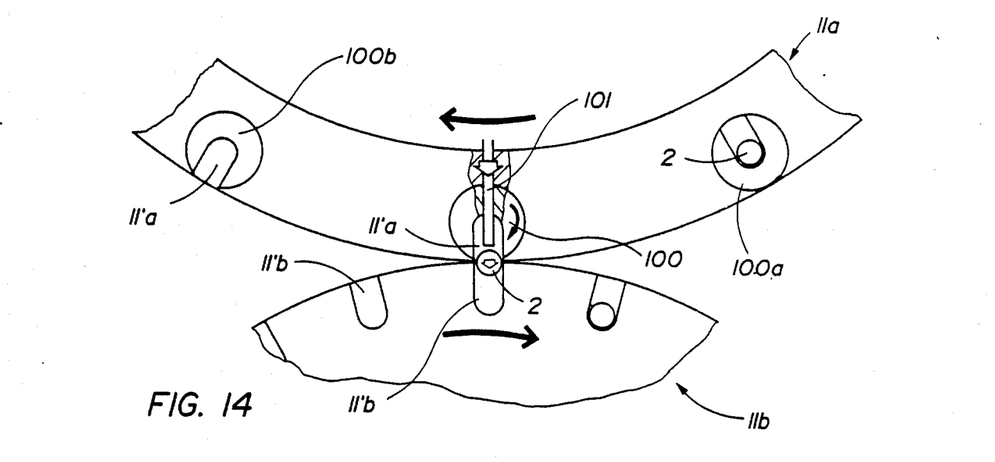
FIG. 14 represents a mode of transfer of the ampoules from a first central unit to a second transport unit.

FIG. 14 illustrates means for transferring the ampoules 2 from a central support and transfer unit 11a to a second transport unit 11b. To allow this transfer, each of these two elements 11a and 11b respectively comprises peripheral recesses 11'a and 11'b. Given that the gassing operation, in order to be effective, requires that the ampoules be momentarily accomodated in a cylindrical cavity with a depth greater than the height of said ampoules, the recesses 11a must be equipped with means permitting them to be closed off. These means may consist of rotary doors 100 represented in a closed position (reference 100a) and in an open position (reference 100b). A pusher 101 acts on the ampoule 2 to drive it from the recess 11'a to the recess 11'b brought facing the recess 11'a by means of the reversed rotations of the two elements 11a and 11b.

The rotary doors 100 may likewise be replaced by any other closing device for example a shutter door or a guillotine slide, a fixed external guide, etc. Opening of the doors and control of the ejector may be achieved by any mechanical means known per se such as a cam, guide ramp, electromagnetic device etc.

Setting the injector in place on the ampoule, and more particularly the phase which begins as soon as the second sealing point is reached (see FIG. 4c), leads to a reduction of the internal volume available for the selected gas overlying the liquid medicine. This volume reduction will result in compression of the selected gas. If the volume reduction due to insertion of the injector is not sufficient to produce an appreciable overpressure within the ampoule, one may, as previously mentioned, increase the overpressure, either during, or after filling the ampoule, during a pressure application phase.

Such an overpressure, which is particularly easy to obtain and to maintain due to the original design of the described syringe, is put to advantage, as will be described in greater detail below, to ensure final control of the syringes after their filling and setting the injectors in place on the ampoules.

Independently of the problem of final control, the overpressure is justified because it permits to obtain and maintain saturation of the liquid medicine with the selected gas, which is usually carbon dioxide. During the well known filling of ampoules with medicine to be injected, one generally saturates the medicine with carbonic gas at room temperature close to 18° to 20° C. One thus obtains a fixed known saturation. Knowing that the medicine behaves approximately like water and that water absorbs substantially its own volume of carbonic gas at 15° C., to increase the saturation one may cool the medicine at the time it is filled. However, this solution is not applicable to all medicines some of which can not be preserved at temperatures lower than 15° C.

The other solution to increase saturation consists in raising the pressure. In practice, to avoid that a given overpressure when assembling the injector with the ampoule, after having filled the latter at a given temperature, may be totally neutralized in the course of storage of the syringe, as a result of a temperature drop leading to an increase in the degree of saturation, the intial overpressure should be determined so that the residual overpressure remains above zero whatever the conservation temperature of the medicine may be.

Another object of the overpressure is to obtain squashing of the stoppering member which results in reinforced tightening of this member against the walls of the ampoule neck. This tightening has the effect of improved sealing of the ampoule and thereby increases the duration of conservation of the medicine it contains, since the conditions of oversaturation with the selected gas are maintained for a longer time.

Figure 15:
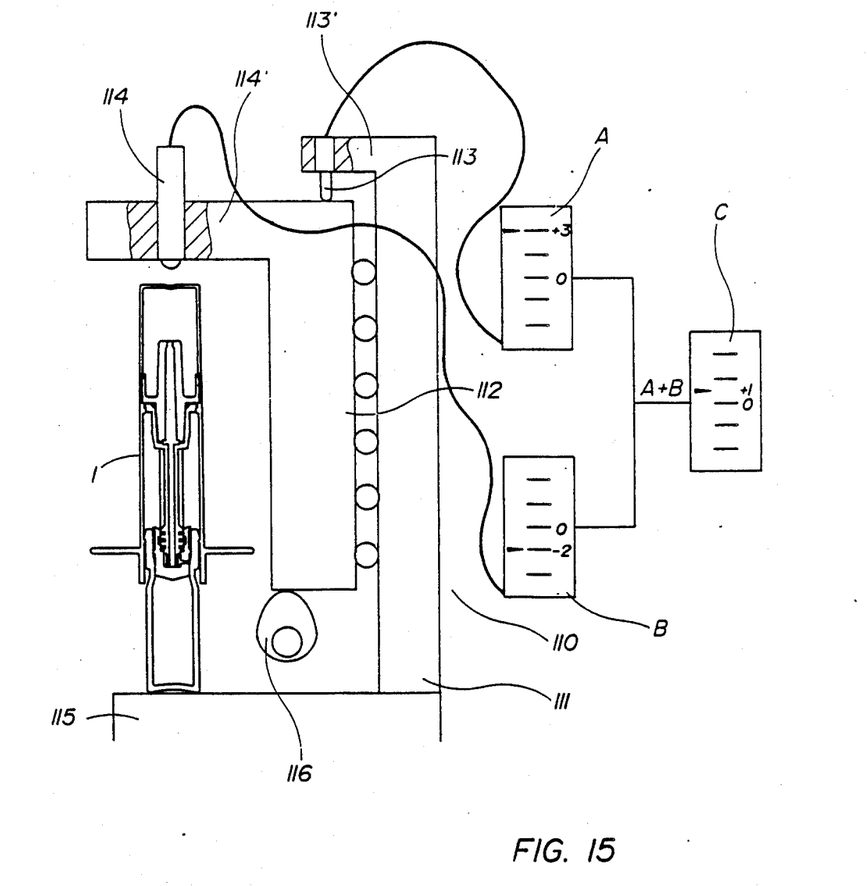
FIG. 15 represents a schematic view of a preferred embodiment of the dynamic control unit for effecting the final control of the syringes.

The station 19 for final control of the syringes or dynamic control station is illustrated in detail in FIG. 15. The device 110 comprises a vertical frame 111, a slide 112 movable along this frame, and two dimension sensor heads 113 and 114 respectively carried by two brackets 113' and 114' respectively solid with the frame and with the slide. The vertical frame is mounted on a support 115 arranged to receive the syringe for said control. A cam 116 controls the displacements of the side with respect to the frame.

The control principle is based on the existence within any conforming syringe of an overpressure of known value. A force exerted on the ampoule—the injector bearing on the support 115, or on the injector, the ampoule bearing on this support—causes a relative penetration of the injector with respect to the ampoule. Due to the overpressure prevailing in the ampoule, elimination of the overpressure of the force having caused this penetration results in a return of the injector to its initial position.

This principle permits the control of a whole series of parameters relating to the syringe components, their assembly and their contents. Thanks to this dynamic control, 100% operation of the syringes is guaranteed, which allows one to quite safely eliminate the visual control of the syringes such as is currently being applied to ampoules. It may be recalled that a complementary safety is obtained by the presence of a filter in each syringe, which filter permits the pharmaceutical industry to guarantee a conforming product even after storage for very long periods.

The control apparatus operates in the following manner: the slide 112 descends until the sensor head or probe 114 comes into contact with the injector. At this moment, the sensor head 114 is depressed with respect to the bracket 114' of the slide. The sensor head 113 being borne on the slide, comes out progressively as the slide descends with respect to the bracket 113'.

During the stroke of the sensor head 114, a data processing unit, connected to this sensor head, sets to zero the memory which records the difference of the values previously recorded by the two dimension sensor heads. When the sensor head 114 has completely penetrated into the bracket 114', this bracket enters into contact with the injector. It is then that a force F corresponding to an inertia weight of mass M sets upon this component which penetrates into the ampoule, the displacement being partly opposed by the overpressure (if the syringe conforms). The difference of the heights indicated by the two sensors remains nil as long as the sensor head 114 remains within the corresponding bracket 114'. As soon as the force F acts upon the injector, the sensor head 113 records a displacement of the slide. The corresponding value is displayed on an indicator A. When the cam arrives at its lowest point, the mass M acts completely upon the injector. When the cam begins to rise again, in a first phase, the sensor head 114 remains within the bracket 114'. At the end of the rise of the injector, the sensor head 114 begins to emerge from the bracket 114'. This end of the rise of the injector is measured by the sensor head 114 and displayed on an indicator B.

An indicator C displays the value of the algebraic sum of the respective values displayed by the indicators A and B, which allows to control by directly reading the possible difference between the descent and the rise of the injector which has been subjected to a given axial thrust.

The dynamic control device described above allows the control of:

(a) the presence of each of the syringe components,
(b) the filling volume,
(c) defective sealing through loss of gas,
(d) silicone coating of the components,
(e) the stoppering member tolerances,
(f) the ampoule tolerances,
(g) assembly of the injector,
(h) sliding of the injector with respect to the ampoule.

Insufficient penetration which causes automatic rejection of the syringe, may be due to the following reasons:

(a) absence of one of the components,
(b) deficient silicone coating of the ampoule,
(c) seizing due to a too small inner diameter of the ampoule, (d) seizing due to a too large outer diameter of the ampoule, (e) too large outer diameter of the stoppering member, (f) too small inner diameter of the capsule, (g) too great volume of filling, (h) unsatisfactory sliding of the injector with respect to the ampoule.

Too great penetration of the injector with respect to the ampoule may be due to the following reasons:

(a) too large inner diameter of the ampoule, (b) too small outer diameter of the stoppering member, (c) a defect of the stoppering member, (d) a defect of the ampoule, (e) an insufficient volume of filling, (f) incorrect assembly of the injector on the ampoule.

If the return movement of the injector beyond its initial position is too great, either the ampoule or the capsule presents a defect, or the injector is incorrectly assembled with the ampoule.

If the return movement of the injector is less than its initial penetration, sealing of the syringe is doubtful, its filling is incorrect or faults in the tolerances of the components cause seizing of the injector with respect to the ampoule.

It may be observed that this control device permits practically all of the parameters of the syringe and its components to be examined. The control station 19 is equipped with means permitting all syringes to be automatically rejected which do not correspond to the predetermined criteria. The accepted syringes satisfy the strictest requirements, so that they are ready for use and do not necessitate any supplementary control.

The principle of the control device based on the utilization of dimension sensor heads and an inertia weight of given mass acting upon the injector, might be replaced by other principles of measurement based on the use of pressure gauges, optical sensors, or the like.

Figure 16:
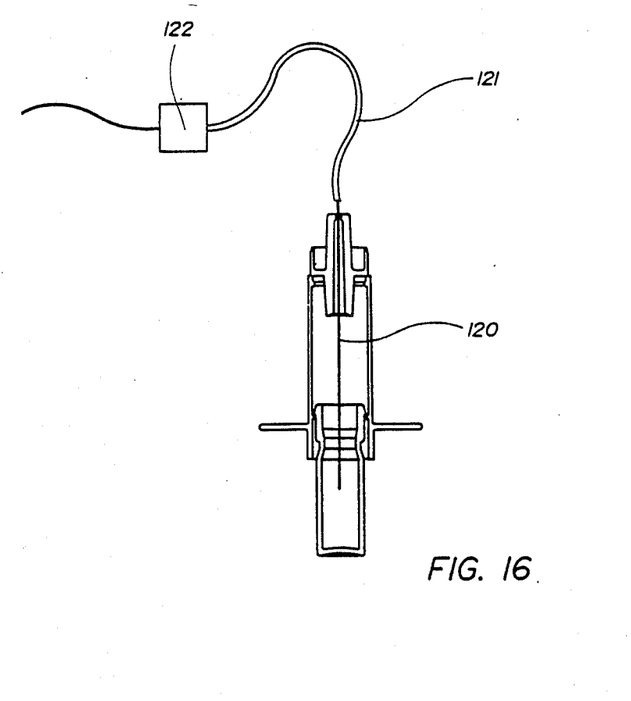
FIG. 16 illustrates an apparatus permitting quantitative control of gassing to be effected.

FIG. 16 illustrates an apparatus permitting statistical control of the amount of gas contained in the ampoule to be effected after assembly of the components. The corresponding station is designated by the reference 20 in FIG. 3. The control is effected in the following manner: a syringe is taken off from time to time. A needle 120 is introduced into the axial channel of the injector, and the stoppering member is pierced so that the free end of the needle reaches the space which is disposed above the liquid and contains the selected gas under pressure. This needle is connected by a flexible tube 121 to a volumetric sensor 122, or more simply to a water column, permitting measurement of the quantity of gas contained in the ampoule.

Figure 17:
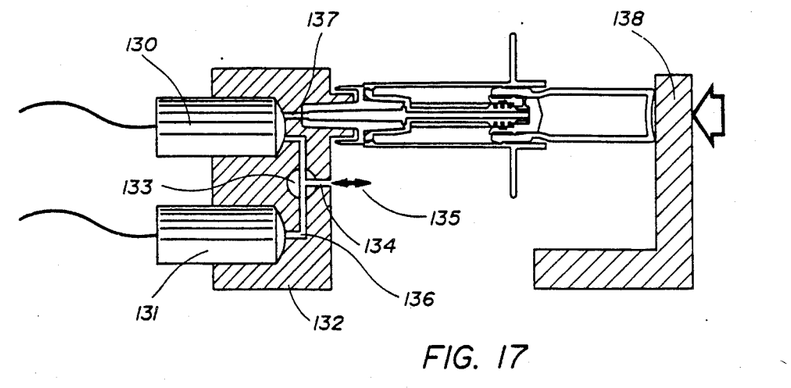
FIG. 17 illustrates an apparatus permitting qualitative control of gassing to be effected.

FIG. 17 illustrates an apparatus permitting to effect statistical control of the quality of the gas contained in the ampoule. This apparatus comprises a particle counter 130 and a gas partial pressure detector 131. The particle counter 130, of the optical or filter type, allows control of the possible existence of solid particles in the selected gas contained in the ampoule. The detector 131 is utilized, in this case, to detect the possible presence of oxygen. It may be of the type commercially available under the denomination ORBISPHERE Model 2715 of ORBISPHERE LABORATORIES (Geneva - Switzerland). This device may be mounted in the station 21 represented schematically in FIG. 3. The two sensors are mounted in a support block 132 comprising a valve 133, a duct 134 for connecting this valve with a supply of selected gas, utilized to vent the installation, indicated by the double arrow 135, a connecting duct 136 providing communication of this valve with the two sensors, and a conduit 137 for connecting the syringe 1 with the sensors. The valve 133 allows the installation to be vented. A pusher 138 exerts a thrust on the ampoule to permit the gas to escape through the channels of the injector successively to the two sensors.

The only method of detecting the presence of oxygen currently used is that of the KOH bath which is impossible to use on a syringe assembly line in an automatic control station.

Utilization of the above method permits achieving an effective, immediately exploitable control of the quality of the gas contained in the ampoules.

The present invention is not limited to the described embodiments and arrangements but may undergo various modifications and may present various variants obvious to one skilled in the art.

We claim:

1. A method of manufacturing a prefilled single-dose syringe comprising an ampoule with a neck of constricted section, for containing a liquid medicine to be injected, and an injector composed of a capsule adapted to engage said ampoule neck and a piston-valve fixed to said capsule and adapted for insertion into said ampoule, said method comprising the steps of:

(a) conveying said injector and said ampoule prefilled with a dose of medicine to be injected, to an assembling station;

(b) positioning said injector above said ampoule and bringing them together for assembly in said station;

(c) subjecting at least said ampoule to a gassing operation prior to assembly of said ampoule and injector in said station, by producing within a cavity entirely enclosing said ampoule an ascending stream of gas sweeping over the outer wall surfaces of said ampoule and by creating a flow of gas sweeping through said injector;

(d) subjecting said gas to qualitative and/or quantitative gas control during or after said gassing operation; and (e) subjecting said syringe to a final control operation, after assembling said ampoule and said injector, by applying a given force to one of said ampoule and injector so as to produce a relative movement thereof with respect to the other and by controlling the return movement thereof to its initial position after having released said force applied thereto, whereby to hermetically seal the syringe with a gas in said ampoule free of contaminants and free of oxygen.

2. Method as in claim 1, wherein said injector has an axial channel and a radial channel, and wherein at least one phase for gassing the injector comprises sweeping said channels with an ascending stream of a gas which intially rises above the liquid contained in the ampoule, and which is later expelled toward said channels when the injector is set in place.

3. Method as in claim 2, wherein said ascending gas stream sweeping the outer walls of the ampoule has a speed which is greater than the speed of a laminar flow in said cavity, and which is capable of keeping away contaminating particles.

4. Method as in claim 2, wherein the sweeping gas stream is produced by delivering into the cavity containing the ampoule a predetermined amount of a selected gas stored in a measuring chamber.

5. Method as in claim 2, wherein the sweeping gas stream is produced by continuously supplying a selected gas to the cavity containing the ampoule.

6. Method as in claim 4, wherein said cavity containing the ampoule is closed off, and the sweeping gas stream is thus produced at a pressure greater than atmospheric pressure.

7. Method as in claim 5, wherein said cavity containing the ampoule is closed off, and the sweeping gas stream is thus produced at a pressure greater than atmospheric pressure.

8. Method as in claim 2, wherein the injector is gassed by creating a descending sweeping gas stream through said channels of the injector, during at least one phase of the operation.

9. Method as in claim 8, wherein the injector is maintained in a chamber containing a selected gas while it is set in place on the ampoule.

10. Method as in claim 1, wherein the quantity and quality of the gas are controlled statistically by punctual test interventions at a determined frequency.

11. Method as in claim 1, wherein said final control of the syringes is effected by exerting a given force axially on the ampoule or on the injector which have been previously assembled, and wherein the value of the relative penetration of these two components and the value of the return movement of these components to their initial position are both determined.

12. Method as in claim 11, wherein the algebraic sum of the two values of the relative penetration and the return movement of said components to their initial position is determined.

13. Method as in claim 11, wherein said given force is exerted with an inertia weight of predetermined mass.

14. Apparatus for manufacturing a prefilled single-dose syringe including an ampoule and an injector, said apparatus comprising:
(a) means for gassing said ampoule and said injector before or after assembling said ampoule and said injector, said means being arranged to produce within a cavity containing the entire ampoule an ascending stream of gas sweeping the outer wall surfaces of the ampoule and to produce a sweeping gas stream through the injector;
(b) means for effecting qualitative and/or quantitative control of the gas during or after gassing; and
(c) means for effecting a final control of the syringe, after assembly of the ampoule and the injector, said final control means being arranged to apply a force to or on one of said ampoule and injector and to control at least the return movement thereof to its initial position.

15. Apparatus as in claim 14, wherein said gassing cavity has a depth greater than the height of said ampoule, and including means for bringing a selected gas into said cavity and means for producing a sweeping stream of this gas, circulating from the bottom upwards between the walls of said cavity and those of the ampoule.

16. Apparatus as in claim 15, wherein said gassing cavity includes a measuring chamber arranged under the gassing cavity, supplied with a selected gas and initially containing a predetermined volume of this gas at a given pressure.

17. Apparatus as in claim 15 wherein said gassing cavity is arranged in a central support and transfer unit, and wherein said central unit is in the form of a circular rotating table or a rectilinear, linearly displaceable table.

18. Apparatus as in claim 17, wherein said central support and transfer unit comprises several cavities each comprising a recess provided at the periphery of said unit and including means for selectively closing off this recess to form a cylindrical cavity.

19. Apparatus as in claim 18, wherein said central support and transfer unit is divided into two adjacent blocks one of which is fixed and the other is mobile in translation, each of these blocks comprising a series of recesses disposed in such a manner that they may be brought to face one another so that at least one of the ampoules, injectors and syringes may be transferred from one recess to another and linearly displaced with said block which is mobile in translation.

20. Apparatus as in claim 18, wherein said central support and transfer unit is associated with a second transport unit, and comprises a series of peripheral recesses each having a rotary door adapted to cooperate with the corresponding recess to form said gassing cavity.

21. Apparatus as in claim 14, wherein said final control means comprise two dimension sensor heads one of which is mounted on a fixed support frame and the other on a slide which is axially mobile with respect to said fixed support frame.

22. Apparatus as in claim 21, wherein said final control means comprise three indicators arranged to indicate respectively the relative penetration of the ampoule and the injector, the return movement of the injector with respect to the ampoule and the algebraic sum of the two previous values.

23. Apparatus as in claim 14, wherein said means for effecting quantitative control of the gas contained in the ampoule comprise a volume gauge and means for providing communication between the interior of the ampoule and said gauge.

24. Apparatus as in claim 14, wherein said means for effecting qualitative control of the gas contained in the ampoule comprise a particle counter and/or a partial gas pressure detector.

25. Apparatus as in claim 14, wherein said gassing cavity is connected to a partial gas pressure detector and/or a particle counter.

* * * * *